US012734279B2

(12) United States Patent
Takatsuji et al.

(10) Patent No.: US 12,734,279 B2
(45) Date of Patent: Sep. 15, 2026

(54) BIOABSORBABLE MEDICAL MATERIAL

(71) Applicants: Kureha Corporation, Tokyo (JP); NATIONAL UNIVERSITY CORPORATION KOBE UNIVERSITY, Hyogo (JP)

(72) Inventors: Kazuhisa Takatsuji, Tokyo (JP); Ayako Fujieda, Tokyo (JP); Sumie Goto, Tokyo (JP); Yoshiki Machi, Tokyo (JP); Junya Hirata, Tokyo (JP); Hironao Shimada, Tokyo (JP); Rieko Hirata, Tokyo (JP); Fujio Sekine, Tokyo (JP); Yusuke Yamashita, Tokyo (JP); Takehiro Sato, Tokyo (JP); Mie Akanuma, Tokyo (JP); Takumi Fukumoto, Hyogo (JP)

(73) Assignees: KUREHA CORPORATION, Tokyo (JP); NATIONAL UNIVERSITY CORPORATION KOBE UNIVERSITY, Kobe (JP)

( * ) Notice: Subject to any disclaimer, the term of this patent is extended or adjusted under 35 U.S.C. 154(b) by 779 days.

(21) Appl. No.: 17/907,336

(22) PCT Filed: Mar. 31, 2021

(86) PCT No.: PCT/JP2021/013973
§ 371 (c)(1),
(2) Date: Sep. 26, 2022

(87) PCT Pub. No.: WO2021/201150
PCT Pub. Date: Oct. 7, 2021

(65) Prior Publication Data

US 2023/0119326 A1 Apr. 20, 2023

(30) Foreign Application Priority Data

Mar. 31, 2020 (JP) ................................ 2020-064458

(51) Int. Cl.
*A61L 31/04* (2006.01)
*A61L 15/28* (2006.01)
*A61L 27/20* (2006.01)

(52) U.S. Cl.
CPC ............. *A61L 31/042* (2013.01); *A61L 15/28* (2013.01); *A61L 27/20* (2013.01); *A61L 2300/424* (2013.01)

(58) Field of Classification Search
CPC ........ A61L 31/042; A61L 15/28; A61L 27/20; A61L 2300/424; A61L 31/129; A61L 31/148; A61K 47/36; A61K 47/34; A61K 47/38
See application file for complete search history.

(56) References Cited

U.S. PATENT DOCUMENTS

| | | | | |
|---|---|---|---|---|
| 4,582,865 | A | 4/1986 | Balazs et al. | |
| 4,605,691 | A | 8/1986 | Balazs et al. | |
| 4,636,524 | A | 1/1987 | Balazs et al. | |
| 5,128,326 | A | 7/1992 | Balazs et al. | |
| 5,532,221 | A | 7/1996 | Huang et al. | |
| 6,294,202 | B1 * | 9/2001 | Burns | A61L 31/041 424/443 |
| 6,521,223 | B1 | 2/2003 | Calias et al. | |
| 6,703,041 | B2 | 3/2004 | Burns et al. | |
| 2002/0018813 | A1 | 2/2002 | Burns et al. | |
| 2002/0071855 | A1 | 6/2002 | Sadozai et al. | |
| 2018/0021477 | A1 | 1/2018 | Isono et al. | |
| 2020/0215079 | A1 * | 7/2020 | Yang | A61K 47/14 |

FOREIGN PATENT DOCUMENTS

| | | | |
|---|---|---|---|
| CN | 105194739 | A | 12/2015 |
| JP | 02-138346 | A | 5/1990 |
| JP | 05-124968 | A | 5/1993 |
| JP | 08-208706 | A | 8/1996 |
| JP | 2003-518167 | A | 6/2003 |
| JP | 2003-523237 | A | 8/2003 |
| JP | 2004-051531 | A | 2/2004 |
| JP | 2008-155014 | A | 7/2008 |
| JP | 2014-65681 | A | 4/2014 |
| WO | 2001046265 | A | 6/2001 |

(Continued)

OTHER PUBLICATIONS

Extended European Search Report for corresponding European Application No. 21781747.7, dated Feb. 23, 2024.

(Continued)

*Primary Examiner* — Susan T Tran
*Assistant Examiner* — William Craigo
(74) *Attorney, Agent, or Firm* — Birch, Stewart, Kolasch & Birch, LLP

(57) ABSTRACT

An embodiment of the present invention is to provide a bioabsorbable medical material having adhesiveness to a biological tissue and improved degradability. A bioabsorbable medical material according to an embodiment of the present invention contains a crosslinked polymer material forming a specific shape, and a disintegration delaying material retained by the crosslinked polymer material. The crosslinked polymer material has degradability in water, the degradability being suppressed in the presence of an acid. The disintegration delaying material releases 0.5 mol %/day or greater of an acid until the seventh day upon contact with water at 37° C.

3 Claims, 2 Drawing Sheets

(56) References Cited

FOREIGN PATENT DOCUMENTS

| | | | | |
|---|---|---|---|---|
| WO | 2016/136884 A1 | | 9/2016 | |
| WO | WO-2019056751 A1 | * | 3/2019 | ............. A61K 1/165 |

OTHER PUBLICATIONS

Noda et al., "Two-Step Sustained-Release PLGA/Hyaluronic Acid Gel Formulation for Intra-articular Administration," Biol. Pharm. Bull., vol. 41, 2018, pp. 937-943.

Nagai et al., "Hydrolytic Degradation of Low Molecular Weigh Poly(Lactic Acid)s and Their Drug Eluting Behavior," Journal of the Society of Materials Science, Japan, vol. 60, No. 1, 2011, pp. 2-7, with a partial English translation.

Japanese Office Action for Japanese Application No. 2023-188861, dated Jan. 7, 2025, with an English translation.

Kang, Sun-Woong, et al., "PLGA Microspheres in Hyaluronic Acid Gel as a Potential Bulking Agent for Urologic and Dermatologic Injection Therapies", Journal of Microbiology and Biotechnology, Jun. 2005, vol. 15, No. 3, pp. 510-518, abstract, fig. 1, 3, 5, materials and methods.

Lin, Xunxun et al., "Hyaluronic Acid Coating Enhances Biocompatib ility of Nonwoven PGA Scaffold and Cartilage Formation", Tissue Engineering: Part C, 2017, vol. 23, No. 2, pp. 86-97, https://doi.org/10.1089/ten.tec.2016.0373, entire text, all drawings.

R.V.Sparer, N.Ekwuribe, A.G.Walton, "Controlled release from glycosaminoglycan drug complexes. In: Controlled Release Delivery Systems", Dekker New York(1983), p. 107-119.

English translation of International Preliminary Report on Patentability and Written Opinion of the International Searching Authority for International Application No. PCT/JP2021/013973, dated Oct. 13, 2022.

Japanese Office Action for Japanese Application No. 2023-188861, dated Oct. 8, 2024, with English translation.

Japanese Office Action for corresponding Japanese Application No. 2022-512650, dated Jun. 6, 2023, with English translation.

European Communication pursuant to Article 94(3) EPC for European Application No. 21 781 747.7, dated Jan. 3, 2025.

European Communication pursuant to Article 94(3) EPC for European Application No. 21 781 747.7, dated Feb. 9, 2026.

* cited by examiner

BIOABSORBABLE MEDICAL MATERIAL

TECHNICAL FIELD

The present invention relates to a bioabsorbable material for medical use.

BACKGROUND ART

Polyanionic polysaccharides, such as hyaluronic acid, carboxynethyl cellulose, or alginic acid, exhibit excellent solubility in water, adequate viscosity, adhesiveness, moisture-retaining property, and biocompatibility. Thus, the polyanionic polysaccharides are widely used as food additives, medical materials, cosmetics, and additives and thickeners of articles for daily use. Among the polyanionic polysaccharides, hyaluronic acid is a commonly and widely used compound.

Hyaluronic acid is a water-soluble polymer and has good dispersibility and water-retaining property, and thus is used in various fields, such as food, cosmetics, and medical and pharmaceutical products. Furthermore, hyaluronic acid is natural mucopolysaccharide, exists in tissues such as vitreous humor, blood vessel walls, and umbilical cords, and thus highly safe, Thus, hyaluronic acid is also widely used in the medical field. Hyaluronic acid is used as a raw material for a joint function improving agent or adhesion-preventing material in the medical field. However, it is difficult to keep hyaluronic acid at a freely chosen position in a body or on a surface of a body for a certain period of time because of its water solubility. Thus, depending on the use such as wound dressing or adhesion prevention, some sort of insolubilization treatment is required to be performed on the hyaluronic acid.

For the insolubilization treatment of hyaluronic acid, a method for insolubilization by crosslinking reaction utilizing a carboxyl group present in the hyaluronic acid molecule has been reported. According to R. V Sparer et al., modification of hyaluronic acid by bonding a cysteine residue to hyaluronic acid through an amide bond and forming a disulfide bond between cysteine residues bonded to the cysteine-modified hyaluronic acids to crosslink the hyaluronic acids is described (Non-Patent Document 1).

In addition, the following various methods have been reported as methods for insolubilization or structural reinforcement. As the known techniques, the following have been reported.

(1) Patent Document 1 describes a method of producing a water-insoluble derivative of a polyanionic polysaccharide, such as hyaluronic acid and carboxymethyl cellulose, by crosslinking reaction using carbodiimide.

(2) Patent Document 2 describes an adhesion-preventing material in which a carboxyl group-containing polysaccharide has undergone water-insolubilization by forming an ionic bond between carboxyl group-containing polysaccharides, such as hyaluronic acid, using a multivalent-cation.

(3) Patent Document 3 describes a method of crosslinking polysaccharides such as hyaluronic acid, protein, or a water-soluble polymer with divinyl sulfone.

(4) In addition, Patent Documents 4, 6, and 7 describe methods of reinforcing a structure by combining biodegradable and absorbable synthetic polymers regardless of presence of crosslinking of polysaccharides.

CITATION LIST

Patent Document

Patent Document 1: JP 2003-518167 T
Patent Document 2: JP 05-124968 A
Patent Document 3: JP 02-138346 A
Patent Document 4: WO 2016/136884
Patent Document 5: JP 2004-051531 A
Patent Document 6: JP 08-208706 A
Patent Document 7: CN 105194739 A Specification

Non-Patent Literature

Non-Patent Document 1: R. V Sparer, N. Ekwuribe, A. G. Walton. Controlled release from glycosaminoglycan drug complexes. In: Controlled Release Delivery Systems. Dekker New York (1983) p. 107-119.

SUMMARY OF INVENTION

Technical Problem

However, with the method described in Patent Document 1, the carboxyl group in the polyanionic polysaccharides undergoes amidation using an amino acid methyl ester. Because water-insolubility of the resulting derivative is enhanced due to this amidation, it is conceived that there is a possibility for the derivative to remain for a long period of time when the derivative is retained in a body. Furthermore, Patent Documents 2 and 3 have no description of the degree of water-insolubility of the resulting film and the like. Furthermore, Patent Document 4 does not include sufficient study on biodegradability control of the biodegradable polymer to be used for reinforcement of a structure, and thus it is conceived that there is a possibility for the biodegradable polymer to remain in a body for a long period of time.

The water-insolubilization-treated polyanionic polysaccharides are reported to have effects as medical materials for wound dressing, adhesion-preventing materials, prosthetic materials, or raw materials thereof in the medical field, and are used in medical sites. Practically, approximately one week is required from the time of covering on and around a wound surface in a body with an adhesion-preventing material to the time when the wound is healed. The adhesion-preventing material preferably maintains a barrier layer such as a film without dissolving during this time period.

Patent Document 5 reports that, when the dissolution half-life of a water-insolubilization-treated carboxymethyl cellulose is short, adequate adhesion prevention performance cannot be exhibited even when application is performed on and around a wound surface in a body. Meanwhile, the decomposition period of the bioabsorbable material in a body varies depending on the raw material constituting the bioabsorbable material, but many literatures point out that a foreign-body reaction occurs due to the bioabsorbable material staying in a body for a long period of time and thus inflammation or the like is caused.

The present invention was completed in light of the problems of these known techniques, and an object of the present invention is to provide a medical material which exhibits effect of wound healing or adhesion prevention by retaining a shape for a period of time necessary to heal injury on a surface of an injured part, where wound healing or adhesion prevention is desirable, with which the entire composition is rapidly absorbed after the injury healing, and which has minimal risk of a foreign-body reaction, inflammation, or infection due to remaining for a long term.

Solution to Problem

As a result of study on the problems described above, the present inventors found a configuration of a medical material crosslinked by covalent bonding and having superior shape retention characteristics compared to untreated or physically crosslinked polysaccharides and proteins when the medical material is retained in a body, or a medical material having less risk of a foreign-body reaction and the like due to remaining for a long term and having excellent degradability compared to polysaccharides or proteins that are combined with a polymer for reinforcement. The gist of embodiments of the present invention are as follows.

(1) A bioabsorbable medical material containing:
- a crosslinked polymer material forming a specific shape, and a disintegration delaying material retained by the crosslinked polymer material,
- the crosslinked polymer material having degradability in water, the degradability being suppressed in the presence of an acid, and
- the disintegration delaying material releasing 0.5 mol %/day or greater of an acid upon contact with water at 37° C. until the seventh day.

(2) The bioabsorbable medical material according to (1), where the crosslinked polymer material covers at least a part of the disintegration delaying material,
- the disintegration delaying material contains an acid releasing material upon contact with water,
- acid releasing ability during a seven-day period after the acid releasing material is immersed in water at 37° C. is 0.3 mol %/day or greater, and
- the crosslinked polymer material contains a polyanionic polymer having a plurality of anionic substituents in a molecule.

(3) The bioabsorbable medical material according to (2), where the acid releasing material is a biodegradable polyester.

(4) The bioabsorbable medical material according to (3), where a number average molecular weight of the biodegradable polyester is 1000 Da or greater and less than 30000 Da.

(5) The bioabsorbable medical material according to (3) or (4), where a content of the biodegradable polyester is 3 wt % or greater with respect to a dry weight of the bioabsorbable medical material.

(6) The bioabsorbable medical material according to any one of (3) to (5), where the biodegradable polyester is polyglycolic acid or a copolymer containing a structural unit derived from glycolic acid.

(7) The bioabsorbable medical material according to any one of (1) to (6), where the crosslinked polymer material is a crosslinked polyanionic polysaccharide.

(8) The bioabsorbable medical material according to any one of (1) to (7), where the crosslinked polymer material contains hyaluronic acid and carboxymethyl cellulose.

(9) The bioabsorbable medical material according to any one of (1) to (8), where the bioabsorbable medical material is a wound dressing material, a tissue regeneration material, a substrate for controlled release of a pharmaceutical, a spacer, or an adhesion-preventing material.

Advantageous Effects of Invention

The bioabsorbable medical material according to an embodiment of the present invention swells by rapidly absorbing water originated from a body and adheres to tissues when applied to a target part of the body. Thus, disintegration of the structure of the medical material is suppressed by the acid generated by the contact of the disintegration delaying material and water. Accordingly, a bioabsorbable medical material that can maintain a desired function for a predetermined period of time in a body is provided. As described above, an embodiment of the present invention can provide a medical material which exhibits effect of wound healing or adhesion prevention by retaining a shape for a period of time necessary to heal injury on a surface of an injured part, where wound healing or adhesion prevention is desirable, with which the entire composition is rapidly absorbed after the injury healing, and which has minimal risk of a foreign-body reaction, inflammation, or infection due to remaining for a long term.

DESCRIPTION OF EMBODIMENTS

Figure 1:
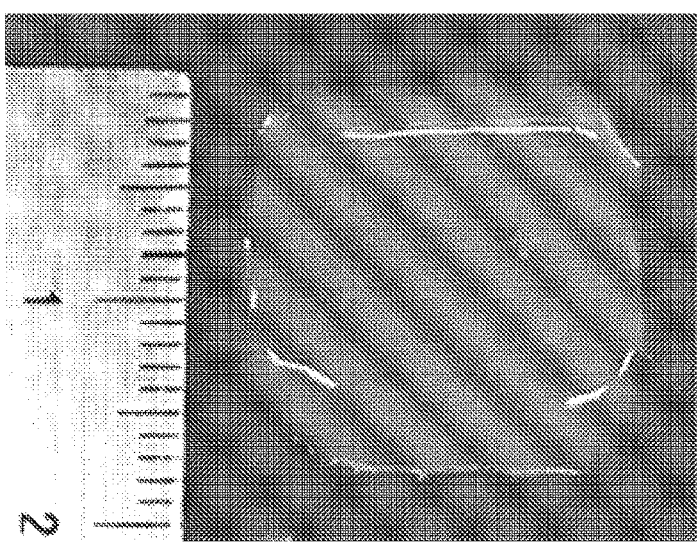
FIG. 1 is a photograph of a typical external appearance with a score of 2 in external appearance evaluation in an example of the present invention.

Embodiments of the present invention will be described in detail below, but the present invention is not limited to the following embodiments.

A bioabsorbable medical material according to an embodiment of the present invention contains a crosslinked polymer material forming a specific shape, and a disintegration delaying material retained by the crosslinked polymer material. For example, the bioabsorbable medical material according to an embodiment of the present invention (hereinafter, also referred to as "bioabsorbable material") contains a disintegration delaying material releasing an acid and a crosslinked polymer material covering at least a part of the disintegration delaying material. The crosslinked polymer material contains, for example, a polyanionic polymer having a plurality of anionic substituents in a molecule.

1. Crosslinked Polymer Material

The crosslinked polymer material contained in the bioabsorbable material according to an embodiment of the present invention has degradability in water. The degradability is suppressed in the presence of an acid. Furthermore, the crosslinked polymer material may be a polymer compound in a state capable of crosslinking, may be a polymer compound that has been already crosslinked, or may include both polymer compounds. The crosslinked polymer material can be appropriately selected among polymer compounds having these properties. One type or more of crosslinked polymer materials may be employed.

The crosslinked polymer material contained in the bioabsorbable material according to an embodiment of the present invention may contain a polyanionic polymer. The polyanionic polymer has a plurality of anionic substituents, such as a carboxy group and a hydroxy group, in a molecule. The polyanionic polymer can be obtained by, as necessary, chemically modifying a polymer compound with anionic substituents. By introducing a cationic substituent to the polyanionic polymer, physical crosslinking can be formed. Based on the state of formed physical crosslinking, various physical properties, such as water-solubility and mechanical properties, of the polyanionic polymer can be adjusted.

Although a physically crosslinked polyanionic polymer is less likely to be hydrated compared to physically uncrosslinked polyanionic polymer, the physically crosslinked polyanionic polymer does not have water-insolubility to the degree that can maintain the structure until an injured part in a body is healed. However, the present inventors found that the presence of an acid contributes to maintenance of the crosslinked structure. When a physically crosslinked polyanionic polymer is implanted in a body, the crosslinking structure is disintegrated due to neutralization or hydration by a cationic ion or a water molecule, and water solubility is increased. However, in the presence of an acid, the anionic substituents, which are the starting point of the crosslinking such as a carboxy group, are less likely to be neutralized or hydrated, and thus the crosslinking structure is maintained.

Examples of the polyanionic polymer include many examples at the present time, at which various chemical modification methods have been developed. From the perspective of high biocompatibility and bioabsorbability, the polyanionic polymer is preferably polyanionic polysaccharides, proteins, or polyamino acids.

Crosslinked Polyanionic Polysaccharide

In one embodiment of the present invention, the physically crosslinked polyanionic polymer is preferably a crosslinked polyanionic polysaccharide. The polyanionic polysaccharide in the present specification means a polysaccharide having a plurality of negatively charged anionic functional groups, such as carbonyl groups, in a molecule. The polyanionic polysaccharides include salts thereof, such as alkali metal salts including sodium salts and potassium salts and alkaline earth metal salts including calcium salts or magnesium salts. Examples of the natural polyanionic polysaccharides include pullulan, alginic acid, hyaluronic acid, chondroitin sulfuric acid, dextran sulfuric acid, and pectin. Examples of the polyanionic polysaccharides synthesized by artificially introducing an anionic group include carboxymethyl amylose, carboxymethyl cellulose, carboxymethyl dextran, carboxymethyl starch, sulfated cellulose, and sulfated dextran. From the perspective of safety in a body and ease in handling, the polyanionic polysaccharides are preferably alginic acid, hyaluronic acid, carboxymethyl cellulose, or carboxymethyl amylose. These polyanionic polysaccharides can be used alone or in combination of two or more types.

The crosslinked polyanionic polysaccharide is a crosslinked product of polyanionic polysaccharide having a structure obtained by subjecting the polyanionic polysaccharide described above to crosslinking treatment. Examples of the crosslinking treatment method of the polyanionic polysaccharide include methods such as ultraviolet radiation treatment, heat treatment, and crosslinking agent treatment. The crosslinking agent treatment is preferred. The crosslinking agent used in the crosslinking agent treatment is preferably a compound having a cationic substituent from the perspective of physically crosslinking the polyanionic polymer. Examples of such a crosslinking agent include carbodiimide, triazine, and imidazole. Specific examples of the carbodiimide include ethyl-3-(3-dimethylaminopropyl)carbodiimide (EDC), N,N'-dicyclohexylcarbodiimide, N,N'-diisopropylcarbodiimide, and N-cyclohexyl-N'-(2-morpholinoethyl) carbodiimide metho-p-toluenesulfonic acid, and the EDC that can be used in an aqueous solvent is more preferred.

As an example of the method of crosslinking agent treatment, first, a polyanionic polysaccharide is dissolved in water or an aqueous solution, and then a crosslinking agent is added thereto and agitated. When the EDC is used as the crosslinking agent, the reaction is proceeded at a low pH in order to allow the carboxyl group of the polyanionic polysaccharide to be an acid type while ensuring high stability of the EDC. This more efficiently ends the reaction. The pH should be preferably from 4.0 to 5.5, Because the pH increases during the reaction, for example, the pH is preferably adjusted by using an acid, such as 0.01 M hydrochloric acid.

The EDC, which is a preferred crosslinking agent, reacts with an anionic substituent, such as carboxylic acid, contained in the polyanionic polysaccharide molecule. By the present reaction, a mixture of N-acylurea that is relatively stable and O-acylisourea that is unstable in water is formed. By the present reaction, a cationic substituent is introduced to the molecule of the polyanionic polysaccharide. By this introduction, the intermolecular interaction between the polyanionic polysaccharides is increased, and a physically crosslinked gel-like polyanionic polysaccharide (crosslinked polyanionic polysaccharide) is obtained.

Protein or Polyamino Acid

In another embodiment of the present invention, the crosslinking polymer material is preferably a protein or a polyamino acid. Examples of the protein include gelatin, collagen, albumin, fibrin, and chemically modified compounds of these. Furthermore, examples of the polyamino acid include polyglutamic acid having an anionic substituent and polyaspartic acid. Among these protein or polyamino acid, acid-treated gelatin is preferred. The acid-treated gelatin has carboxyl groups formed by subjecting acid amides to hydrolysis in its production process, and thus has a plurality of anionic substituents in a molecule. Similarly to the polyanionic polysaccharide, by chemically modifying an anionic substituent and introducing a cationic substituent to the anionic substituent, physically crosslinked gelatin can be obtained.

2. Disintegration Delaying Material

The disintegration delaying material contained in the bioabsorbable material of an embodiment of the present invention releases an acid in not less than a specific amount per unit time for a particular period of time upon contact with water. The release period and the release ability of an acid of the disintegration delaying material can be appropriately selected based on the use for a body. From the perspective of such use, upon contact with water at 37° C., the release period of an acid is seven days, and the release ability of the acid is 0.5 mol %/day or greater. The release ability is only required to be achieved for at least one day in the release period (seven days) of the acid and is preferably achieved for the entire period.

The beginning and ending of the acid release period are not limited. The beginning of the release period of the acid may be at the time of contact with water at 37° C. or may be after a predetermined period of time has passed from the contact. The lower limit of the release ability of the acid may be appropriately selected in a range that satisfies 0.5 mol %/day or greater, based on the use for a body of the bioabsorbable material of an embodiment of the present invention. For example, for the use for wound adhesion prevention in a body, the disintegration delaying material releases 0.5 mol %/day or greater of an acid until the seventh day upon contact with water at 37° C. The amount of acid to be released until the seventh day may be 2.0 mol %/day or greater, and may be 3.5 mol %/day or greater.

The upper limit of the release ability of an acid is not limited from the perspective of suppressing disintegration of the crosslinked polymer material. The upper limit of the release ability of the acid may be appropriately selected based on the use for a body of the bioabsorbable material of an embodiment of the present invention. For example, from the perspective of suppressing occurrence of inflammation reaction in a body, the upper limit is preferably 40 mol %/day or less, and more preferably 20 mol %/day or less, after the first day.

The acid release ability can be measured by titration of an aqueous dispersion of the disintegration delaying material using 1,8-diazabicyclo[5.4.0]-7-undecene (DBU), as described in Examples below. Furthermore, the release ability of an acid can be adjusted for a certain degree based on the type or molecular weight of the disintegration delaying material, and a smaller molecular weight tends to make the release ability of an acid higher.

The disintegration delaying material contained in the bioabsorbable material of an embodiment of the present invention contains a material releasing an acid upon contact with water. The acid releasing material is a material releasing an acid in a sustained manner, and specifically a material having a release ability of an acid during a seven-day period after immersed in water at 37° C. of 0.3 mol %/day or greater. The lower limit of the release ability during the seven-day period after the material is immersed in water at 37° C. may be appropriately selected in a range that satisfies 0.3 mol %/day or greater, based on the use for a body of the bioabsorbable material of an embodiment of the present invention. For example, for use in wound adhesion prevention in a body, the acid releasing ability of the disintegration delaying material during the seven-day period after the disintegration delaying material is immersed in water at 37° C. may be 1.0 mol %/day or greater, or 1.3 mol %/day or greater.

The release ability of an acid is represented by percentage of an amount of substance of an acid released in water at 37° C. with respect an amount of substance of an acid contained in the acid releasing material. When the acid is contained in the acid releasing material as an acid precursor forming the acid by hydrolysis, the release ability of the acid is represented by dividing the percentage of amount of substance of an acid released in water at 37° C. with respect to an ideal amount of substance of an acid generated when all the acid precursor described above is hydrolyzed by the number of days passed.

The release ability of an acid during a seven-day period can be determined by dividing a value of the acid releasing ability converted based on the measured value of the acid concentration during the seven-day period upon contact with water at 37° C. by the number of days of measurement interval by which the measured value was obtained. When the acid concentration was measured multiple times during the seven-day period, the acid releasing ability value can be determined as an acid releasing ability value from the previous time to this time, and in this case, the release ability of the acid during the seven-day period can be determined as a release ability value in a freely chosen period among the measured values up to the seventh day.

By allowing the acid releasing material contained in the disintegration delaying material to have the characteristics described above, when the bioabsorbable material is placed at a predetermined position of a body and the disintegration delaying material is brought into contact with water in the body, the disintegration delaying material can continuously release the acid. Accordingly, the crosslinking structure of the crosslinked polymer material is maintained and the disintegration thereof is suppressed, and the desired functions can be maintained for a predetermined period of time. For example, when the bioabsorbable material is an adhesion-preventing material, by placing the adhesion-preventing material between internal organs, the adhesion between the organs in the body can be suppressed. The acid releasing material is preferably a release controlling material or a biodegradable polyester described below.

Release Controlling Material

As an embodiment of the present invention, the acid releasing material may be a release controlling material containing a carrier and an acid, and having a function to perform controlled release of an acid upon contact with water Examples of the acid include acetic acid, propionic acid, malic acid, succinic acid, phthalic acid, and maleic acid. When the content of the acid is not less than a specific amount relative to the dry weight of the bioabsorbable material, higher effect of maintaining the structure of the crosslinking polymer material is expected.

Examples of the release controlling material include a composition (coating) in which powder of an acid is covered by a carrier, and a solid dispersion in which microparticles or molecular state of an acid are dispersed in a carrier.

The powder of an acid to be coated is not limited to the powder consisting only of the acid. The powder of an acid to be coated may be powder obtained by forming a layer of the powder of an acid using a carrier particle, such as refined sugar, lactose, D-mannitol, corn starch, or crystalline cellulose, as a nucleus. Alternatively, the powder of an acid to be coated may be powder obtained by immersing the carrier particles described above in a liquid acid or an acid solution and, optionally, volatilizing the solvent. A composition, in which such an acid powder is covered by a carrier, may be used as the release controlling material.

The carrier may contain one or both of a water-soluble material and a water-insoluble material. As a carrier to be used for covering (hereinafter, also referred to as "coating agent"), a water-soluble coating agent can be used. The water-soluble coating agent dissolves when brought into contact with water. By removing the cover by the carrier, a contained acid is released.

Furthermore, as a carrier to be used for covering, a water-insoluble coating agent can be also used. As the water-insoluble coating agent, a material having water permeability when used as a covering material is preferred. By allowing the covering material to have water permeability, water infiltrates into the release controlling material through the cover formed of the water-insoluble coating agent. The acid contained in the release controlling material is dissolved by the infiltrating water. The acid aqueous solution formed by the dissolution is released to the outside from the inside of the release controlling material by permeating through the cover. Examples of the water-insoluble coating agent that can form the cover with water permeability include a polymer having a mesh structure larger than the molecule of the contained acid, a porous inorganic material, and a porous polymer material.

Furthermore, even when a cover with water permeability cannot be obtained by a water-insoluble coating agent alone, a cover with water permeability can be obtained by the combined use of a water-insoluble coating agent and a water-soluble coating agent. That is, when a cover formed by mixing a water-insoluble coating agent and a water-soluble coating agent is brought into contact with water, only the water-soluble coating agent is removed. This removal makes it possible to provide a cover with water permeability, the cover being formed of the water-insoluble coating agent and having a plurality of cavities communicating with the release controlling material surface and the contained acid. The miscibility of the water-soluble coating agent and the water-insoluble coating agent is appropriately adjusted by a mixing ratio between the water-soluble coating agent and the water-insoluble coating agent or selection of the water-soluble coating agent and the water-insoluble coating agent. By this, the size or shape of the cavities of the cover, the cavities being formed by contact with water, can be adjusted and, as a result, release of the acid can be controlled.

Alternatively, the release controlling material may contain a carrier having cavities with interconnected cells. In the release controlling material, the acid is contained in the cavities of the carrier. The carrier may be a material having a porous structure by the cavities described above, and can be appropriately selected in a range that does not substantially interact with a body. With such a release controlling material, for example, by adjusting the size or shape of the cavities as described above, release of the acid can be controlled.

The solid dispersion can be prepared by drying a solution, in which a carrier and an acid are dissolved together by a method such as spray drying, heat drying, hot-air drying, vacuum drying, and freeze-drying. The solid dispersion can be also prepared by cooling after an acid is dispersed in a melted carrier.

An identical material can be used for the coating agent and the carrier for the solid dispersion. Examples of the material for the coating agent include refined sugar, lactose, D-mannitol, corn starch, crystalline cellulose, talc, precipitated sodium carbonate, gelatin, gum arabic, pullulan, povidone, copolyvidone, hydroxypropyl cellulose, hypromellose, polyvinyl acetal diethylamino acetate, aminoalkyl methacrylate copolymers, cellulose acetate phthalate, methacrylic acid copolymer L, methacrylic acid copolymer LD, methacrylic acid copolymer S, hydroxypropyl methylcellulose phthalate, hydroxypropyl methylcellulose acetate succinate, carboxyethyl cellulose, ethylcellulose, polyvinylcaprolactam-polyvinyl acetate-polyethylene glycol graft copolymers, hydrogenated oil, carnauba wax, aminoalkyl methacrylate copolymer RS, polyvinyl alcohol-acrylic acid-methyl methacrylate copolymers, and ethyl acrylate-methyl methacrylate copolymer emulsions.

Biodegradable Polyester

In another embodiment of the present invention, the acid releasing material is preferably a biodegradable polyester. The content of the biodegradable polyester of 3 wt % or greater relative to the dry weight of the bioabsorbable material is preferred because higher effect of maintaining the structure of the crosslinking polymer material is exhibited.

From the perspective of absorption speed of the crosslinked polymer material and controlled release of an acid in a body, the biodegradable polyester is preferably a composition containing a biodegradable polyester having a low molecular weight, and specifically, a biodegradable polyester having a number average molecular weight of less than 30000 dalton (Da) is preferably contained. By allowing at least 3 wt % of the biodegradable polyester having a molecular weight of less than 30000 dalton to be contained with respect to the dry weight of the bioabsorbable material, disintegration of the crosslinked structure of the crosslinked polymer material can be appropriately suppressed. The biodegradable polyester having a low molecular weight has a high hydrolysis speed compared to a biodegradable polyester having a high molecular weight, and can release a desired amount of an acid rapidly. The released acid suppresses disintegration of the crosslinked structure of the crosslinked polymer material, and also acts as a catalyst of decomposition reaction of the biodegradable polyester itself (autocatalytic action). Thus, the biodegradable polyester having a low molecular weight can promote continuous release of an acid.

The number average molecular weight of the biodegradable polyester is preferably 1000 Da or greater from the perspective of setting the release period of an acid in a body adequately long. As described above, the number average molecular weight of the biodegradable polyester can be a means to adjust to a desired release period of an acid corresponded to desired use of the bioabsorbable material.

In addition to the biodegradable polyester having a low molecular weight, the acid releasing material may contain a biodegradable polyester having a molecular weight of 50000 Da or greater to reinforce the bioabsorbable material. Even when the biodegradable polyester having a molecular weight of 50000 Da or greater is contained, decomposition of the biodegradable polyester having a large molecular weight can be promoted due to the autocatalytic action by the biodegradable polyester having a low molecular weight preferably contained in the bioabsorbable material of the present embodiment. Thus, even when the biodegradable polyester having a molecular weight of 50000 Da or greater is contained, long term remaining of the material constituting the bioabsorbable material in a body is suppressed.

From the perspectives described above, the molecular weight distribution of the biodegradable polyester preferably has bimodal distribution, and the number average molecular weight of the biodegradable polyester preferably has peaks at 1000 Da or greater and less than 50000 Da, and 50000 Da or greater and 500000 Da or less. At this time, the proportion of the biodegradable polyester having a molecular weight of 1000 Da or greater and less than 50000 Da in the biodegradable polyester is preferably 3 weight % (3 wt %) or greater, more preferably 5 wt % or greater, even more preferably 10 wt % or greater, and most preferably 20 wt % or greater, from the perspective of suppressing long term remaining in a body described above.

The form of the biodegradable polyester can be freely selected but is preferably in a fiber form, a pulverized form, or a mixture form of these. The fiber form includes any fibrous materials such as short fibers, long fibers, monofilaments, multifilaments, and nonwoven fabric. Examples of the pulverized form include particles and powders.

As the biodegradable polyester, specifically, polyglycolic acid releasing an acid when hydrolyzed, polylactic acid, polycaprolactone, polydioxanone, and copolymers of these are preferred. Among these, a glycolic acid homopolymer (polyglycolic acid) having a short bioabsorption period or a copolymer containing a structural unit derived from glycolic acid is preferred, and a glycolic acid homopolymer is most preferred.

3. Method of Producing Bioabsorbable Material

The shape of the bioabsorbable material of an embodiment of the present invention can be appropriately selected in a range that allows application to a body, and examples thereof include sheet-like, powder-like, and gel-like or sol-like that contains a protonic solvent. A sheet-like bioabsorbable material can be obtained as a continuous film or porous sheet-like material by, for example, pouring a liquid mixture, solution, or dispersion of a crosslinking polymer material and a disintegration delaying material into an appropriate container, followed by air-drying or freeze-drying.

The obtained sheet-like material may be heat-treated by using a hot press device. By the heat treatment, a bioabsorbable material having further enhanced insolubility in water can be obtained. Accordingly, a period of time, in which the structure is maintained in a body, can be made longer while flexibility of the bioabsorbable material is maintained. From the perspectives of external appearance and handling, the heat treatment temperature is preferably from 80° C. to 150° C. Furthermore, adjustment (e.g., enhancement) of the insolubility in water can be also performed by the content, thickness, or the like of the disintegration delaying material, or by the concentration of a crosslinking agent when the crosslinked polymer material is a crosslinked polyanionic polysaccharide, without employing the heat treatment.

4. Use of Bioabsorbable Material

The bioabsorbable material of an embodiment of the present invention is useful as a medical material used mainly in a body because the disintegration of the structure is suppressed until the injured part is healed when retained in a body and risk of inflammation and the like due to remaining for a long term is small. The period of remaining of the bioabsorbable material of an embodiment of the present invention in a body can be appropriately adjusted by a combination of the crosslinked polymer material and the disintegration delaying material. Although it cannot be generalized, the beginning of the decomposition of the bioabsorbable material of an embodiment of the present invention in a body can be adjusted between the time of application to a biological tissue to 7 days after the application. The period of decomposition of the bioabsorbable material of an embodiment of the present invention in a body can be adjusted between a period of 7 days to 14 days. The ending of the decomposition of the bioabsorbable material of an embodiment of the present invention in a body can be adjusted between the time of application to a biological tissue to 14 days to 28 days after the application. Note that, the "decomposition" described above means a state in which the condition of the bioabsorbable material in a body or in an environment simulating inside the body is changed to a degree that can be visually observed. "Beginning of decomposition" is a first time at which the condition change described above is confirmed, and "ending of decomposition" is a first time at which the condition change described above is no longer confirmed.

The bioabsorbable medical material of an embodiment of the present invention that is dried can swell and adhere upon absorption of moisture. Thus, when the bioabsorbable medical material of an embodiment of the present invention is applied to a wound part in a body caused by endoscopic submucosal dissection or the like, a moist environment appropriate for wound healing is maintained by suppressing retention of exudate and, at the same time, stimuli from the outside are blocked. Thus, the bioabsorbable medical material of an embodiment of the present invention can be used as a covering material in a body for preventing ulceration or preventing perforation.

Furthermore, when the bioabsorbable medical material of an embodiment of the present invention contains a pharmaceutical such as growth factor or antimicrobial agent, and placed in a body, the bioabsorbable medical material decomposes in a body, and as the structure disintegrates, the pharmaceutical is released in a controlled manner around the placed position. Thus, the bioabsorbable medical material of an embodiment of the present invention can be used as a substrate for controlled release of a pharmaceutical.

Furthermore, the structural material of the bioabsorbable medical material of an embodiment of the present invention has high biocompatibility and bioabsorbability. Thus, by using the bioabsorbable medical material of an embodiment of the present invention to a part partially losing biological tissues in a body, the bioabsorbable medical material can be also used as a tissue regeneration material aiming at replacement of own tissues.

Furthermore, the sheet-like bioabsorbable medical material of an embodiment of the present invention functions as a barrier layer suppressing transport of cells and components within a body with respect to the covered face by absorbing moisture and swelling when implanted in the body. Thus, the bioabsorbable medical material of an embodiment of the present invention can be used as an adhesion-preventing material.

Furthermore, the bioabsorbable medical material of an embodiment of the present invention can maintain the form in a body for a particular period of time. Thus, the bioabsorbable medical material of an embodiment of the present invention can be used as a spacer to hold a space formed by biological tissues by, for example, applying the bioabsorbable medical material to a wall surface of a tubular structure forming a space in a body.

EXAMPLES

Embodiments of the present invention will be described specifically below based on examples, but the present invention is not limited to these examples.

1. Measurement of Acid Releasing Ability

As the raw materials for the biodegradable polyester, powder and fibers of polyglycolic acid (PGA), powder of copolymer of DL-lactic acid and glycolic acid (PLGA), and powder of polylactic acid (PLA) listed below were prepared. For the raw materials of polyglycolic acid, polyglycolic acids having various molecular weights and commercially available polyglycolic acid suture were prepared.

PGA-P1: PGA powder (Mn: 11000 Da, particle size: 38 μm or less)

PGA-P2: PGA powder (Mn: 3000 Da, particle size: 38 μm or less)

PGA-P3: PGA powder (Mn: 31000 Da, particle size: 38 μm or less)

PGA-P4: PGA powder (Mn: 71000 Da, particle size: 38 μm or less)

PGA-P5: PGA powder (Mn: 200000 Da, particle size: 38 μm or less)

PGA-F1: Commercially available PGA suture ("SURGISORB" available from BEAR Medic Corporation ("SURGISORB" is a trade name of Nitcho Kogyo K.K., number: 3-0)

PLGA-P1: Commercially available PLGA powder ("RESOMER RG 752H" available from SIGMA ("RESOMER" is a trade name of Evonik); unit ratio: lactic acid 75: glycolic acid 25; Mn: 4000 to 15000 Da)

PLGA-P2: Commercially available PLGA powder ("RESOMER RG 502H" available from SIGMA; unit ratio: lactic acid 50: glycolic acid 50; Mn: 7000 to 17000 Da)

PLA-P1: Commercially available PLA powder ("RESOMER R202H" available from SIGMA; Mn: 10000 to 18000 Da)

Samples each containing 16.7 mg of the biodegradable polyester material described above dispersed in 16 mL of ultrapure water at 37° C. were prepared, and the acid concentration when a particular time passed after preparation of the sample was measured. Note that the sample of PGA-P1 was prepared by dispersing 13 mg of PGA-P1 in 12.4 mL of ultrapure water. The sample of PGA-F1 was cut into a length of approximately 2 mm and used. The sample of PLGA-P1 was prepared by dispersing 19.7 mg of PLGA-P1 in 16 mL of ultrapure water. The sample of PLGA-P2 was prepared by dispersing 18.7 mg of PLGA-P2 in 16 mL of ultrapure water. The sample of PLA-P1 was prepared by dispersing 20.7 mg of PLA-P1 in 16 mL of ultrapure water. The acid concentration was measured by titration using 1,8-diazabicyclo[5.4.0]-7-undecene (DBU). The DBU having the concentration confirmed in advance by titration using 0.01 M HCl was used. As described above in the description of the release ability of an acid, the acid releasing ability was calculated by dividing the percentage of amount of substance of an acid released in water at 37° C. with respect to an ideal amount of substance of an acid generated when all the biodegradable polyester material described above is hydrolyzed when a particular time passed by the number of days passed. The results are shown in Table 1.

In the table below, "PEs material" refers to the raw material of the biodegradable polyester described above, "Ca" refers to acid concentration (mmol/L), and "Ar" refers to acid releasing ability (mol %/day). Furthermore, ΔAr was calculated by determining the difference between acid concentrations of consecutive days (e.g., day t0 to day t1), converting it into the acid releasing ability, and dividing the acid releasing ability by the number of measurement days thereof. More specifically, LAr was calculated by determining a difference Cal between acid concentration on day t1 and acid concentration on day t0, converting the Cal into the acid releasing ability Ar1, and dividing the Ar1 by a difference Δt between t1 and t0. Note that, in Table 1 "*" indicates "not performed", and "**" indicates that calculation was not performed because the molecular weight of the suture was unknown. Note that, in Table 1 ΔAr of 24 hours is not shown because the ΔAr is the same as Ar in the table.

TABLE 1

Acid concentration and acid releasing ability

| PEs material | TIME ELAPSED (HOURS) 24 Ca | 24 Ar | 72 Ca | 72 Ar | 72 ΔAr | 120 Ca | 120 Ar | 120 ΔAr |
|---|---|---|---|---|---|---|---|---|
| PGA-P1 | 0.759 | 4.21 | 1.730 | 3.20 | 2.69 | 2.298 | 2.55 | 1.58 |
| PGA-P2 | 2.964 | 16.58 | 3.497 | 6.52 | 1.49 | 3.954 | 4.42 | 1.28 |
| PGA-P3 | 0.128 | 0.71 | 0.238 | 0.44 | 0.30 | 0.420 | 0.47 | 0.51 |
| PGA-P4 | 0.037 | 0.20 | 0.077 | 0.14 | 0.11 | 0.108 | 0.12 | 0.09 |
| PGA-P5 | 0.011 | 0.06 | 0.020 | 0.04 | 0.03 | 0.021 | 0.02 | 0.00 |
| PGA-F1 | —* | —* | —* | —* | —* | —* | —* | —* |
| PLGA-P1 | 0.020 | 0.11 | 10.040 | 0.07 | 0.06 | 0.115 | 0.13 | 0.21 |
| PLGA-P2 | 0.006 | 0.03 | 0.075 | 0.14 | 0.19 | 0.148 | 0.17 | 0.21 |
| PLA-P1 | 0.017 | 0.09 | 0.028 | 0.05 | 0.03 | 0.025 | 0.03 | 1-0.01 |

| PEs material | TIME ELAPSED (HOURS) 168 Ca | 168 Ar | 168 ΔAr | 240 Ca | 240 Ar | 240 ΔAr | 336 Ca | 336 Ar | 336 ΔAr |
|---|---|---|---|---|---|---|---|---|---|
| PGA-P1 | 2.709 | 2.15 | 1.14 | 3.460 | 1.92 | 1.39 | 4.402 | 1.74 | 1.30 |
| PGA-P2 | 4.713 | 3.77 | 2.13 | 5.554 | 3.11 | 1.57 | 6.682 | 2.67 | 1.58 |
| PGA-P3 | 0.812 | 0.65 | 1.09 | 1.505 | 0.84 | 1.29 | 2.434 | 0.97 | 1.29 |
| PGA-P4 | 0.133 | 0.11 | 0.07 | 0.362 | 0.20 | 0.42 | 0.702 | 0.28 | 0.47 |
| PGA-P5 | 0.098 | 0.08 | 0.21 | 0.125 | 0.07 | 0.05 | 0.151 | 0.06 | 0.04 |
| PGA-F1 | 0.007 | —** | —* | —* | —* | —* | 0 | —** | —* |
| PLGA-P1 | 0.495 | 0.39 | 1.06 | 0.826 | 0.46 | 0.62 | 1.063 | 0.42 | 0.33 |
| PLGA-P2 | 0.911 | 0.73 | 2.13 | 1.357 | 0.76 | 0.83 | 2.655 | 1.06 | 1.81 |
| PLA-P1 | 0.086 | 0.07 | 0.17 | 0.073 | 0.04 | −0.02 | 0.032 | 0.01 | −0.06 |

According to Table 1, it was found that PGA-P1 generated 2.71 mmol/L of the acid from the beginning of the test to the seventh day. It was found that PGA-P2 generated 4.71 mmol/L of the acid from the beginning of the test to the seventh day. It was found that PGA-P3 generated 0.81 mmol/L of the acid from the beginning of the test to the seventh day. It was found that PGA-P4 generated 0.13 mmol/L of the acid from the beginning of the test to the seventh day. It was found that PGA-P5 generated 0.10 mmol/L of the acid from the beginning of the test to the seventh day. It was found that PGA-F1 generated 0.01 mmol/L of the acid from the beginning of the test to the seventh day. It was found that PLGA-P1 generated 0.50 mmol/L of the acid from the beginning of the test to the seventh day. It was found that PLGA-P2 generated 0.91 mmol/L of the acid from the beginning of the test to the seventh day. It was found that PLA-P1 generated 0.09 mmol/L of the acid from the beginning of the test to the seventh day. It was found that, after the immersion, the polyglycolic acid having a low molecular weight released 0.3 mol %/day or greater of the acid for 168 hours. Furthermore, the polyglycolic acids having relatively high molecular weights, the commercially available polyglycolic acid, the commercially available PLGA powders, and the commercially available PLA powder did not continuously release 0.3 mol %/day or greater of acids.

2. Preparation of Bioabsorbable Material

Example 1

In 800 mL of ultrapure water, 44 g of sodium hyaluronate (HA, molecular weight: 2200000 Da) was added and dissolved, then 2.0 g of sodium carboxymethylcellulose (CMC; molecular weight: 1500000 Da) was added, and thus a liquid mixture was obtained. While the pH of the liquid mixture was maintained to 4.5 to 5.2 by using 0.1 M HCl, 8.5 g of ethyl-3-(3-dimethylaminopropyl)carbodiimide (EDC) was dissolved in 20 mL of ultrapure water, and the total amount of the solution was added dropwise. After addition of the EDC aqueous solution, agitation and pH adjustment with 0.1 M HCl were performed for 1.5 to 2.0 hours until the pH change of the solution was stabilized. The obtained reaction solution was subjected to dialysis by using a regenerated cellulose dialysis tube (molecular weight cut-off: 12000 to 14000). Low molecular weight components, such as unreacted materials and byproducts, were removed from the reaction solution while the dialysate was exchanged. The dialysate was exchanged 3 times during 36 hours from the start of the dialysis. In this way, a crosslinked HA/CMC solution containing a crosslinked product of HA and/or CMC and EDC was obtained.

In 90 g of the obtained crosslinked HA/CMC solution, 252 mg of PGA-P1 (4 molar equivalents with respect to the number of moles of structural unit of HA) was added, and the PGA-P1 was dispersed. The crosslinked HA/CMC solution to which PGA-P1 was added was poured in a mold formed of glass plate and silicone rubber and having 11 cm length×11 cm width, and air-dried at room temperature. The film obtained by air-drying was heat-treated at 90° C. for 15 minutes and then 120° C. for 10 minutes by using a hot press device, and a film-like PGA/HA/CMC-1 (bioabsorbable material 1) was obtained.

Comparative Example 1

A film-like sample (bioabsorbable material 2) was obtained in the same manner as in Example 1 except for using no PGA-P1.

Comparative Example 2

A commercially available adhesion-preventing material ("Seprafilm" available from Sanofi; "Seprafilm" is a trade name of Baxter) was prepared. This was used as "bioabsorbable material 3".

3. Evaluation (1) Shape Change after Immersion in Phosphate Buffer Solution

In 8 mL of phosphate buffer solution (pH 73), a 1 $cm^2$ sample (dimension: 1 cm×1 cm) of each of bioabsorbable materials 1 to 3 was immersed and stored at 37° C. The external appearance of shape of the sample at 72 h, 120 h, and 168 h after the immersion was observed, and the shape was evaluated. In a case where the following score was 2 or greater, it was determined that a film-like shape was maintained.

For the result of the external appearance observation, one of the following scores was assigned for each of external appearance images of the bioabsorbable materials 1 to 3, and the result was expressed by an average value of the scores judged by a plurality of (five) experienced and skilled technicians while the image was referred.

4 Points: The external appearance was substantially the same as the planar shape of the sample before the immersion.

3 Points: Although the external appearance was overall expanded from the planar shape of the sample before the immersion, presence of the sample was able to be visually confirmed.

2 Points: Although the external appearance was overall expanded from the planar shape of the sample and included somewhat disintegrated part, presence of the sample was able to be visually confirmed.

1 Point: It was confirmed that the external appearance was in an indeterminate form by liquid drop.

0 Points: The external appearance was not confirmed due to dissolution.

Figure 2:
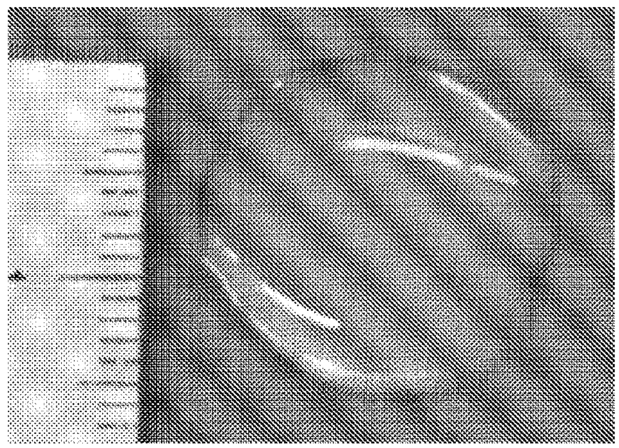
FIG. 2 is a photograph of a typical external appearance with a score of 1 in external appearance evaluation in an example of the present invention.

The results are shown in Table 2. Furthermore, FIG. 1 is a photograph showing a typical external appearance with the score of 2 described above. FIG. 2 is a photograph showing a typical external appearance with the score of 1 described above.

TABLE 2

| | TIME ELAPSED (HOURS) | | |
|---|---|---|---|
| Material No. | 72 | 120 | 168 |
| 1 | 3.0 | 2.0 | 1.0 |
| 2 | 3.0 | 1.0 | 1.0 |
| 3 | 2.6 | 0 | 0 |

From the results of Table 2, the bioabsorbable material 1 maintained the planar shape even 120 hours passed after the immersion, and the shape thereof was not confirmed at the time when 168 hours passed. On the other hand, for the bioabsorbable materials 2 and 3, in which no PGA was added, the shapes thereof were not confirmed at the time when 120 hours passed after the immersion.

In this way, disintegration of the bioabsorbable material 1 was suppressed. The acid releasing ability during the seven-day period of the disintegration delaying material of the bioabsorbable material 1 was at least 0.3 mol %/day to achieve adequate disintegration suppressing effect.

4. Examination of Content of Biodegradable Polyester

Bioabsorbable materials 1-1 to 1-3 were prepared in the same manner as in Example 1 except for changing the added amount of the PGA-P1 to 0.5, 1, and 2 molar equivalents with respect to the number of moles of structural unit of contained HA. Then, evaluation identical to the evaluation of "Shape Change after Immersion in Phosphate Buffer Solution" described above was performed. The results are shown in Table 3. In the table, "PEs content" represents a content of a biodegradable polyester and is a ratio of the number of moles of the biodegradable polyester to the number of moles of structural unit of HA in the bioabsorbable material.

TABLE 3

| Material | PEs | TIME ELAPSED (HOURS) | | |
|---|---|---|---|---|
| No. | content (-) | 72 | 120 | 168 |
| 1-1 | 0.5 | 3.2 | 1.0 | 1.0 |
| 1-2 | 1.0 | 3.4 | 2.0 | 1.0 |
| 1-3 | 2.0 | 3.0 | 2.0 | 1.0 |
| 1 | 4.0 | 3.0 | 2.0 | 1.0 |
| 2 | 0 | 3.0 | 1.0 | 1.0 |

As shown in Table 3, as the added amount of the PGA-P1 in the bioabsorbable material increased, the period of time in which the film shape was maintained increased. It was found that, although it also depends on use of the bioabsorbable material, from the perspective of preventing adhesion to another tissue in a wound, the added amount of the PGA-P1 in the bioabsorbable material is only required to be 1 molar equivalent or greater with respect to the amount of HA, and is only required to be 3 wt % or greater in terms of dry weight of the bioabsorbable material.

5. Verification of Adhesion Prevention Effect

Then, to confirm whether this material exhibits adhesion prevention effect after a surgical operation, the adhesion prevention effect of each material was evaluated by using a rat liver segmentectomy model. First, a bioabsorbable material 1-4 was prepared in the same manner as in Example 1 except for changing the amount of the crosslinked HA/CMC solution to 100 g, and changing the added amount of the PGA-P1 to 3.4 molar equivalents with respect to the number of moles of structural unit of contained HA. Also, a bioabsorbable material 2-1 was prepared in the same manner as in Comparative Example 1 except for changing the amount of the crosslinked HA/CMC solution to 100 g.

Using seven rats as one group, a part of the left lateral lobe of liver of a rat was excised, and the excised face of the liver was covered and adhered closely with the bioabsorbable material 2-1 or the bioabsorbable material 1-4. On the seventh day after the surgical operation, a dissection was performed, and a score was assigned to adhesion between the liver excised face and another tissue as the degree of severity of adhesion (0: no adhesion, 1: adhesion that can be separated by own weight, 2: adhesion that can be separated by blunt dissection, 3: adhesion that requires sharp dissection). The results are shown in Table 4. In Table 4, the numeric value of "score" of the bioabsorbable material 2-1 or the bioabsorbable material 1-4 of "degree of severity of adhesion" represents the number of rats came under the score. The numeric value of "average" is a value calculated by dividing the sum total of products of scores for the bioabsorbable material 2-1 or the bioabsorbable material 1-4 and the number of rats by the number of rats.

TABLE 4

| | Degree of severity of adhesion | | | | |
|---|---|---|---|---|---|
| | Score | | | | |
| Material No. | 3 | 2 | 1 | 0 | Average |
| 1-4 | 1 | 1 | 0 | 5 | 0.7 |
| 2-1 | 3 | 4 | 0 | 0 | 2.4 |

As a result, as shown in Table 4, it was confirmed that the bioabsorbable material 1-4 containing the PGA-P1 had a high adhesion prevention effect.

6. Examination of Crosslinked Polymer Material

By using sodium hyaluronate and pullulan (Pul) in place of sodium carboxymethylcellulose, a crosslinked HA/Pul solution was prepared in the same manner as in the preparation of the crosslinked HA/CMC solution using ethyl-3-(3-dimethylaminopropyl)carbodiimide. In 283 mL of ultrapure water, 1.6 g of sodium hyaluronate was added and dissolved, 0.5 g of pullulan was added, and thus a liquid mixture was obtained. While the pH of the liquid mixture was maintained to 4.5 to 5.2 by using 0.1 M HCl, 3 g of ethyl-3-(3-dimethylaminopropyl)carbodiimide was dissolved in 7 mL of ultrapure water, and the total amount of the solution was added dropwise. Except for this procedure, a bioabsorbable material 4 was obtained in the same manner as in Example 1. The bioabsorbable material 4 is also expected to exhibit disintegration suppression effect by acid release similar to that of the bioabsorbable material 1.

INDUSTRIAL APPLICABILITY

The bioabsorbable medical material of an embodiment of the present invention is useful as an adhesion-preventing material. Furthermore, because the material maintaining and constituting the shape for a particular period of time does not remain for a long period of time, the bioabsorbable medical material can be used for medical use, as a wound dressing material, a tissue regeneration material, a substrate for controlled release of a pharmaceutical, and a spacer.

The invention claimed is:

1. An adhesion-preventing material comprising:

a gel-like polyanionic polysaccharide, and particles or powders of a homopolymer of a glycolic acid retained by the gel-like polyanionic polysaccharide, wherein the gel-like polyanionic polysaccharide comprises a hyaluronic acid that is chemically treated, a number average molecular weight of the particles or the powders of the homopolymer being 1000 Da or greater and less than 30000 Da, and a content of the particles or the powders of the homopolymer is 3 wt % or greater with respect to a dry weight of the bioabsorbable medical material.

2. The bioabsorbable medical material according to claim 1, wherein the particles or the powders of the homopolymer is contained inside the gel-like polyanionic polysaccharide.

3. A method of manufacturing the adhesion-preventing material according to claim 1, comprising:

preparing an aqueous solution containing a chemically treated hyaluronic acid;

preparing particles or powders of the homopolymer of a glycolic acid;

mixing the particles or the powders in the aqueous solution to form a dispersion of the particles or the powders;

casting the dispersion to form a film; and heat-pressing the film at a temperature of 80° C. or higher and 150° C. or lower.

* * * * *